(12) United States Patent
Ackley et al.

(10) Patent No.: US 6,726,880 B1
(45) Date of Patent: Apr. 27, 2004

(54) ELECTRONIC DEVICE FOR PERFORMING ACTIVE BIOLOGICAL OPERATIONS AND METHOD OF USING SAME

(75) Inventors: Donald E. Ackley, Cardiff, CA (US); Paul D. Swanson, Santee, CA (US); Scott O. Graham, San Diego, CA (US); Elizabeth L. Mather, San Diego, CA (US); Timothy L. LeClair, San Diego, CA (US); William F. Butler, La Jolla, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

(21) Appl. No.: 09/596,657

(22) Filed: Jun. 19, 2000

Related U.S. Application Data

(63) Continuation of application No. 09/026,618, filed on Feb. 20, 1998, now Pat. No. 6,099,803, which is a continuation-in-part of application No. 08/753,962, filed on Dec. 4, 1996, now Pat. No. 6,287,517, which is a continuation-in-part of application No. 08/534,454, filed on Sep. 27, 1995, now Pat. No. 5,849,486, which is a continuation-in-part of application No. 08/304,657, filed on Sep. 9, 1994, now Pat. No. 5,632,957, which is a continuation-in-part of application No. 08/271,882, filed on Jul. 7, 1994, now Pat. No. 6,017,696, which is a continuation-in-part of application No. 08/146,504, filed on Nov. 1, 1993, now Pat. No. 5,605,622.

(51) Int. Cl.$^7$ .................. G01N 15/00; G01N 1/00; G01N 33/53; C12Q 1/68
(52) U.S. Cl. .................. 422/68.1; 422/50; 422/129; 435/6; 435/7.1
(58) Field of Search .................. 422/50, 68.1, 129; 435/6, 7.1

(56) References Cited

U.S. PATENT DOCUMENTS

| | | | |
|---|---|---|---|
| 3,950,738 A | 4/1976 | Hayashi et al. | 365/185 |
| 3,995,190 A | 11/1976 | Salgo | 313/391 |
| 4,283,773 A | 8/1981 | Daughton et al. | 364/132 |
| 4,563,419 A | 1/1986 | Ranki et al. | 435/6 |
| 4,580,895 A | 4/1986 | Patel | 356/39 |
| 4,584,075 A | 4/1986 | Goldstein | 204/522 |
| 4,594,135 A | 6/1986 | Goldstein | 204/551 |
| 4,751,177 A | 6/1988 | Stabinsky | 435/6 |
| 4,787,963 A | 11/1988 | MacConnell | 204/450 |
| 4,807,161 A | 2/1989 | Comfort et al. | 364/550 |
| 4,816,418 A | 3/1989 | Mack et al. | 436/518 |
| 4,822,566 A | 4/1989 | Newman | 422/82 |
| 4,828,979 A | 5/1989 | Klevan et al. | 435/6 |
| 4,908,112 A | 3/1990 | Pace | 210/198 |
| 5,063,081 A | 11/1991 | Cozzette et al. | 435/4 |
| 5,074,977 A | 12/1991 | Cheung et al. | 205/775 |
| 5,075,077 A | 12/1991 | Durley, III et al. | 422/56 |
| 5,096,669 A | 3/1992 | Lauks et al. | 422/61 |
| 5,096,807 A | 3/1992 | Leaback | 435/6 |
| 5,125,748 A | 6/1992 | Bjornson et al. | 356/414 |
| 5,126,022 A | 6/1992 | Soane et al. | 204/458 |
| 5,143,854 A | 9/1992 | Pirrung et al. | 436/518 |
| 5,156,810 A * | 10/1992 | Ribi | 422/82.01 |
| 5,164,319 A | 11/1992 | Hafeman et al. | 435/287 |
| 5,166,063 A | 11/1992 | Johnson | 435/173 |
| 5,200,051 A | 4/1993 | Cozzette et al. | 204/403 |
| 5,202,231 A | 4/1993 | Drmanac et al. | 435/6 |
| 5,219,726 A | 6/1993 | Evans | 435/6 |
| 5,227,265 A | 7/1993 | DeBoer et al. | 430/41 |
| 5,234,566 A | 8/1993 | Osman et al. | 204/403 |
| 5,242,797 A | 9/1993 | Hirshfeld | 435/6 |
| 5,304,487 A | 4/1994 | Wilding et al. | 435/29 |
| 5,312,527 A | 5/1994 | Mikkelsen et al. | 205/777 |
| 5,433,819 A | 7/1995 | McMeen | 216/20 |
| 5,434,049 A | 7/1995 | Okano et al. | 435/6 |
| 5,445,525 A | 8/1995 | Broadbent et al. | 439/64 |
| 5,516,698 A | 5/1996 | Begg et al. | 436/89 |
| 5,527,670 A | 6/1996 | Stanley | 435/6 |
| 5,527,681 A | 6/1996 | Holmes | 435/6 |
| 5,605,662 A | 2/1997 | Heller et al. | 422/68 |
| 5,632,957 A | 5/1997 | Heller et al. | 422/68 |
| 5,653,939 A | 8/1997 | Hollis et al. | 422/50 |
| 5,677,195 A | 10/1997 | Winkler et al. | 436/518 |
| 5,681,751 A | 10/1997 | Begg et al. | 436/89 |

FOREIGN PATENT DOCUMENTS

| | | |
|---|---|---|
| EP | 0228075 | 7/1987 |
| GB | 2156074 | 10/1985 |
| GB | 2247889 | 3/1992 |
| WO | WO86/03782 | 7/1986 |
| WO | WO88/08528 | 11/1988 |
| WO | WO89/01159 | 2/1989 |
| WO | WO89/10977 | 11/1989 |
| WO | WO90/01564 | 2/1990 |
| WO | WO92/04470 | 3/1992 |
| WO | WO93/22678 | 11/1993 |
| WO | WO95/07363 | 3/1995 |
| WO | WO96/01836 | 1/1996 |
| WO | WO98/01758 | 1/1998 |
| WO | WO98/51819 | 11/1998 |
| YU | 57087 | 8/1990 |

OTHER PUBLICATIONS

Abrams et al. "Comprehensive Detection of Single Base Changes In Human Genomic DNA Using Denaturing Gradient Gel Electrophoresis & a GC Clamp". *Genomics*, 7, 1990, 463–475.

(List continued on next page.)

Primary Examiner—Ardin H. Marschel
(74) Attorney, Agent, or Firm—O'Melveny & Myers LLP

(57) ABSTRACT

An electronic device for performing biological operations includes a support substrate and an array of microlocations disposed on the substrate. The array of microlocations include electronically addressable electrodes. A first collection electrode is disposed on the substrate and adjacent to a first side of the array of microlocations. A second collection electrode is disposed on the substrate and adjacent to a second side of the array of microlocations, the second side of the array being opposite of the first side such that the array of microlocations is disposed between the first and second collection electrodes. A flow cell is supported on the substrate. Preferably, the combined area of the collection electrodes is a substantial fraction, preferably at least 50% of the area of the footprint of the flow cell.

15 Claims, 12 Drawing Sheets

OTHER PUBLICATIONS

Anand and Southern "Pulsed Field Gel Electrophoresis," *Gel Electrophoresis of Nucleic Acids—A Practical Approach*, 2d. Ed., D. Rickwood and B.D. Hames (New York:IRL Press 1990), pp 101–123.

Anderson and Young, "Quantitative Filter Hybridization," *Nucleic Acid Hybridization—A Practical Approach*, Eds. B.D. Hames and S.J. Higgins (Washington, D.C. :IRL Press 1985) pp 73–111.

Bains, "Setting a Sequence to Sequence a Sequence," *Bio/Technology*, 10:757–758 (1992).

Barinaga, "Will 'DNA Chip' Speed Genome Initiative?", *Science*, 253:1489 (1991).

Beattie et al., "Genosensor Technology," *The 1992 San Diego Conference: Genetic Recognition*, pp 1–5 (Nov., 1992).

Beltz et al., "Isolation of Multigene Families and Determination of Homologies by Filter Hybridization Methods," *Methods in Enzymology*, 100:266–285 (1983).

Brown et al. "Electrochemically Induced Adsorption of Radio–Labelled DNA on Gold and HOPG Substrates for STM Investigations". *Ultramicroscopy*, 38, 1991, 253–264.

Conner et al., "Detection of Sickle Cell $\beta^3$–Globin Allele by Hybridization With Synthetic Oligonucleotides," *Proc. Natl. Acad. Sci. USA*, 80:278–282 (1983).

Drmanac et al., "Sequencing of Megabase Plus DNA by Hybridization: Theory of the Method," *Genomics*, 4:114–128 (1989).

Drmanac et al., "DNA Sequence Determination by Hybridixation: A Strategy for Efficeint Large–Scale Sequencing," *Science*, 260: 1649–1652 (1993).

Eggers et al. "Biochip Technology Development", BioChip Technology Development, Lincoln Laboratory Technical Report 901, Nov. 9, 1990.

Fiaccabrino et al., "Array of Individually Addressable Microelectrodes", Sensors and Actuators B, 18–19 (1994) 675–677.

Fodor et al., "Multiplexed Biochemical Assays With Biological Chips," *Nature*, 364:555–556 (1993).

Fodor et al., "Light–Directed, Spatially Addressable Parallel Chemical Synthesis," *Science*, 251:767–773 (1992).

Horejsi, "Some Theoretical Aspects of Affinity Electrophoresis," *Journal of Chromatography*, 178:1–13 (1979).

Horejsi et al., Determination of Dissociation Constants of Lectin Sugar Complexes by Means of Affinity Electrophoresis, *Biochimica at Biophysica Acta*, 499:200–300 (1977).

Kakerow et al., "A Monolithic Sensor Array of Individually Addressable Microelectrodes", Sensors and Acuators A, 43 (1994) 296–301.

Mathews, Kricka. "Analytical Strategies For The Use Of DNA Probes". *Analytical Biochemistry*, 169, 1988, 1–25.

Palecek, "New Trends in Electrochemical Analysis of Nucleic Acids". *Bioelectrochemistry and Bioenergetics*, 20, 1988, 179–194.

Ranki et al., "Sandwich Hybridization as a Convenient Method for the Detection of Nucleic Acids in Crude Samples," *Gene*, 21:77–85 (1983).

Saiki, "Amplification of Genomic DNA," *PCR Protocols: A Guide to Methods and Applications*, (Academic Press, Inc. 1990), pp 13–20.

Southern et al., "Analyzing and Comparing Nucleic Acid Sequences by Hybridization to Arrays of Oligonucleotides Evaluation Using Experimental Models," *Genomics*, 13:1008–1017 (1992).

Stezoska et al., "DNA Sequencing by Hybridization: 100 Bases Read by a Non–Gel–Based Method", *Proc. Natl. Acad. Sci. USA*, 88:10089–93 (1991).

Wallace et al., "Hybridization of Synthetic Oligodexribonucleotides to $\phi \times 174$ DNA: The Effect of Single Base Pair Mismatch," *Nucleic Acid Res.*, 6:3543–3557 (1979).

Washizu, "Electrostatic Manipulatiaon of Biological Objects," *Journal of Electrostatics*, 25:109–123 (1990).

Washizu and Kurosawa, "Electrostatic Manipulation of DNA in Microfabricated Structures," *IEEE Transactions on Industry Applications*, 26:1165–1172 (1990).

Brown et al., "Electrochemically Induced Adsorption of Radio–Labelled DNA on Gold and HOPG Substrates for STM Investigations", *Ultramicroscopy*, 38 (1991) pp 253–264.

Palecek, "New Trends in Electrochemical Analysis of Nucleic Acids", *Bioelectrochemistry and Bioenergetics*, 20 (1988) pp 179–194.

* cited by examiner

ELECTRONIC DEVICE FOR PERFORMING ACTIVE BIOLOGICAL OPERATIONS AND METHOD OF USING SAME

RELATED APPLICATION INFORMATION

This application is a continuation of application Ser. No. 09/026,618, filed Feb. 20, 1998, now issued as U.S. Pat. No. 6,099,803, which is a continuation-in-part application of application Ser. No. 08/753,962, filed Dec. 4, 1996, entitled "Laminated Assembly for Active Bioelectronic Devices" now issued as U.S. Pat. No. 6,287,517, which is a continuation-in-part of Ser. No. 08/534,454, filed Sep. 27, 1995, entitled "Apparatus and Methods for Active Programmable Matrix Devices" now issued as U.S. Pat. No. 5,849,486, which is a continuation-in-part of application Ser. No. 08/304,657, filed Sep. 9, 1994, entitled, as amended, "Molecular Biological Diagnostic Systems Including Electrodes", now issued as U.S. Pat. No. 5,632,957, continued as Ser. No. 08/859,644, filed May 20, 1997, now issued as U.S. Pat. No. 6,582,660 which is a continuation-in-part of application Ser. No. 08/271,882, filed Jul. 7, 1994, entitled, as amended, "Methods for Electronic Stringency Control for Molecular Biological Analysis and Diagnostics", now issued as U.S. Pat. No. 6,017,696, which is a continuation-in-part of application Ser. No. 08/146,504, filed Nov. 1, 1993, entitled, as amended, "Active Programmable Electronic Devices for Molecular Biological Analysis and Diagnostics", now issued as U.S. Pat. No. 5,605,662, continued as application Ser. No. 08/725,976, filed Oct. 4, 1996 entitled "Methods for Electronic Synthesis of Polymers" now issued as U.S. Pat. No. 5,929,208 and application Ser. No. 08/709,358, filed Sep. 6, 1996, entitled "Apparatus and Methods for Active Biological Sample Preparation" now issued as U.S. Pat. No. 6,129,828, and is related to application Ser. No. 08/846,876, filed May 1, 1997, entitled "Scanning Optical Detection System" now issued as U.S. Pat. No. 6,309,601, all incorporated herein by reference as if fully set forth herein.

FIELD OF THE INVENTION

This invention relates to methods of manufacture and devices useful in performing active biological operations. More particularly, the invention relates to devices containing active electrodes especially adapted for electrophoretic transport of nucleic acids, their hybridization and analysis.

BACKGROUND OF THE INVENTION

Molecular biology comprises a wide variety of techniques for the analysis of nucleic acid and protein. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, *Molecular Cloning: A Laboratory Manual*, 2 Ed., Cold spring Harbor Laboratory Press, Cold Spring Harbor, N.Y., 1989).

Most of these techniques involve carrying out numerous operations (e.g., pipetting, centrifugations, electrophoresis) on a large number of samples. They are often complex and time consuming, and generally require a high degree of accuracy. Many a technique is limited in its application by a lack of sensitivity, specificity, or reproducibility. For example, these problems have limited many diagnostic applications of nucleic acid hybridization analysis.

The complete process for carrying out a DNA hybridization analysis for a genetic or infectious disease is very involved. Broadly speaking, the complete process may be divided into a number of steps and sub-steps. In the case of genetic disease diagnosis, the first step involves obtaining the sample (blood or tissue). Depending on the type of sample, various pre-treatments would be carried out. The second step involves disrupting or lysing the cells, which then release the crude DNA material along with other cellular constituents. Generally, several sub-steps are necessary to remove cell debris and to purify further the crude DNA. At this point several options exist for further processing and analysis. One option involves denaturing the purified sample DNA and carrying out a direct hybridization analysis in one of many formats (dot blot, microbead, microplate, etc.). A second option, called Southern blot hybridization, involves cleaving the DNA with restriction enzymes, separating the DNA fragments on an electrophoretic gel, blotting to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out the polymerase chain reaction (PCR) or other amplification procedure. The PCR procedure amplifies (increases) the number of target DNA sequences relative to non-target sequences. Amplification of target DNA helps to overcome problems related to complexity and sensitivity in genomic DNA analysis. All these procedures are time consuming, relatively complicated, and add significantly to the cost of a diagnostic test. After these sample preparation and DNA processing steps, the actual hybridization reaction is performed. Finally, detection and data analysis convert the hybridization event into an analytical result.

The steps of sample preparation and processing have typically been performed separate and apart from the other main steps of hybridization and detection and analysis. Indeed, the various substeps comprising sample preparation and DNA processing have often been performed as a discrete operation separate and apart from the other substeps. Considering these substeps in more detail, samples have been obtained through any number of means, such as obtaining of full blood, tissue, or other biological fluid samples. In the case of blood, the sample is processed to remove red blood cells and retain the desired nucleated (white) cells. This process is usually carried out by density gradient centrifugation. Cell disruption or lysis is then carried out on the nucleated cells to release DNA, preferably by the technique of sonication, freeze/thawing, or by addition of lysing reagents. Crude DNA is then separated from the cellular debris by a centrifugation step. Prior to hybridization, double-stranded DNA is denatured into single-stranded form. Denaturation of the double-stranded DNA has generally been performed by the techniques involving heating (>Tm), changing salt concentration, addition of base (NaOH), or denaturing reagents (urea, formamide, etc.). Workers have suggested denaturing DNA into its single-stranded form in an electrochemical cell. The theory is stated to be that there is electron transfer to the DNA at the interface of an electrode, which effectively weakens the double-stranded structure and results in separation of the strands. See, generally, Stanley, "DNA Denaturation by an Electric Potential", U.K. patent application 2,247,889 published Mar. 18, 1992.

Nucleic acid hybridization analysis generally involves the detection of a very small number of specific target nucleic acids (DNA or RNA) with an excess of probe DNA, among a relatively large amount of complex non-target nucleic acids. The substeps of DNA complexity reduction in sample preparation have been utilized to help detect low copy numbers (i.e. 10,000 to 100,000) of nucleic acid targets. DNA complexity is overcome to some degree by amplification of target nucleic acid sequences using polymerase chain reaction (PCR). (See, M. A. Innis et al, *PCR Protocols: A Guide to Methods and Applications*, Academic Press, 1990). While amplification results in an enormous number of target nucleic acid sequences that improves the subsequent direct probe hybridization step, amplification involves lengthy and cumbersome procedures that typically must be performed on a stand alone basis relative to the other substeps. Substantially complicated and relatively large equipment is required to perform the amplification step.

The actual hybridization reaction represents one of the most important and central step in the whole process. The hybridization step involves placing the prepared DNA sample in contact with a specific reporter probe, at a set of optimal conditions for hybridization to occur to the target DNA sequence. Hybridization may be performed in any one of a number of formats. For example, multiple sample nucleic acid hybridization analysis has been conducted on a variety of filter and solid support formats (See G. A. Beltz et al., in *Methods in Enzymology*, Vol. 100, Part B, R Wu, L. Grossman, K. Moldave, Eds., Academic Press, New York, Chapter 19, pp. 266–308, 1985). One format, the so-called "dot blot" hybridization, involves the non-covalent attachment of target DNAs to filter, which are subsequently hybridized with a radioisotope labeled probe(s). "Dot blot" hybridization gained wide-spread use, and many versions were developed (see M. L. M. Anderson and B. D. Young, in *Nucleic Acid Hybridization—A Practical Approach*, B. D. Hames and S. J. Higgins, Eds., IRL Press, Washington, D.C. Chapter 4, pp. 73–111, 1985). It has been developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (see M. Barinaga, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application #570/87, 1987; R. Drmanac et al., 4 Genomics, 114, 1989; Strezoska et al., 88 Proc. Natl. Acad. Sci. USA 10089, 1992; and R. Drmanac and R. B. Crkvenjakov, U.S. Pat. No. 5,202,231, Apr. 13, 1993).

There are two formats for carrying out SBH. The first format involves creating an away of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, United Kingdom Patent Application GB 8810400, 1988; E. M. Southern et al., 13 Genornics 1008, 1992, proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array.

Concurrently, Drmanac et al., 260 Science 1649–1652, 1993, used the second format to sequence several short (116 bp) DNA sequences. Target DNAs were attached to membrane supports ("dot blot" format). Each filter was sequentially hybridized with 272 labeled 10-mer and 11-mer oligonucleotides. A wide range of stringency condition was used to achieve specific hybridization for each n-mer probe; washing times varied from 5 minutes to overnight, and temperatures from 0 to 16. Most probes required 3 hours of washing at 16. The filters had to be exposed for 2 to 18 hours in order to detect hybridization signals. The overall false positive hybridization rate was 5% in spite of the simple target sequences, the reduced set of oligomer probes, and the use of the most stringent conditions available.

A variety of methods exist for detection and analysis of the hybridization events. Depending on the reporter group (fluorophore, enzyme, radioisotope, etc.) used to label the DNA probe, detection and analysis are carried out fluorimetrically, colorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. A number of other factors also reduce the sensitivity and selectivity of DNA hybridization assays.

In conventional fluorimetric detection systems, an excitation energy of one wavelength is delivered to the region of interest and energy of a different wavelength is remitted and detected. Large scale systems, generally those having a region of interest of two millimeters or greater, have been manufactured in which the quality of the overall system is not inherently limited by the size requirements of the optical elements or the ability to place them in optical proximity to the region of interest. However, with small geometries, such as those below 2 millimeters, and especially those on the order of 500 microns or less in size of the region of interest, the conventional approaches to fluorimeter design have proved inadequate. Generally, the excitation and emission optical elements must be placed close to the region of interests Preferably, a focused spot size is relatively small, often requiring sophisticated optical designs. Further, because it is usually desirable to maximize the detectable area, the size of the optical components required to achieve these goals in relation to their distance from the region of interest becomes important, and in many cases, compromises the performance obtained. Accordingly, a need exists for an improved fluorescent detection system.

Attempts have been made to combine certain processing steps or substeps together. For example, various microrobotic systems have been proposed for preparing arrays of DNA probe on a support material. For example, Beattie et al., in *The 1992 San Diego Conference: Genetic Recogition*, November, 1992, used a microrobotic system to deposit micro-droplets containing specific DNA sequences into individual microfabricated sample wells on a glass substrate.

Generally, the prior art processes have been extremely labor and time intensive. For example, the PCR amplification process is time consuming and adds cost to the diagnostic assay. Multiple steps requiring human intervention either during the process or between processes is suboptimal in that there is a possibility of contamination and operator error. Further, the use of multiple machines or complicated robotic systems for performing the individual processes is often prohibitive except for the largest laboratories, both in terms of the expense and physical space requirements.

Attempts have been made to enhance the overall sample introduction, to sample preparation analysis process. Given the relatively small volume of sample material which is often times available, improved processes are desired for the efficient provisions of sample, transport of sample and effective analysis of sample. While various proposals have been advanced, certain systems enjoy relative advantages in certain circumstances.

Yet another area of interest is in the electrical addressing of relatively large arrays. As array grow relatively large, the efficient operation of the system becomes more of a consideration. Efficient interfacing of an array based system with electrical connections off-chip raise pin or contact limitation issues. Further, constraints regarding effective chip or array size present issues regarding the selection of components, and the size of them, for inclusion on the chip or substrate. Often times, various selections must be made to provide an effective optimization of advantages in the overall design.

As is apparent from the preceding discussion, numerous attempts have been made to provide effective techniques to conduct multi-step, multiplex molecular biological reactions. However, for the reasons stated above, these techniques are "piece-meal", limited and have not effectively optimized solutions. These various approaches are not easily combined to form a system which can carry out a complete DNA diagnostic assay. Despite the long-recognized need for such a system, no satisfactory solution has been proposed previously.

SUMMARY OF THE INVENTION

Methods of manufacture and apparatus adapted for advantageous use in active electronic devices utilized for biological diagnostics are disclosed. Specifically, various layouts or embodiments, including the selection of components, are utilized in advantageous combination to provide useful devices.

In a first preferred embodiment, an electronic device for performing active biological operations comprises in combination a support substrate, an array of microlocations disposed on the substrate, a first collection electrode disposed on the substrate, first and second focusing electrodes disposed on the substrate, the first and second electrodes being disposed at least in part adjacent the array of microlocations, the distance between the first and second electrodes adjacent the array preferably being smaller than the distance between the first and second electrodes in yet another region disposed away from the array; and counter electrodes disposed on the substrate. In operation of this embodiment, a solution containing DNA or other biological material to be interrogated, are provided to the device, above the substrate. As a typical initial step, the concentration electrode and return electrodes are activated so as to transport and concentrate the charged biological materials onto or near the concentration region. In the preferred embodiment, the concentration electrode and the return electrode or electrodes interrogate a relatively large volume of the sample. Typically, the collection electrode and counter electrodes are disposed on the substrate so that the electrophoretic lines of force are significant over substantially all of the flow cell volume. By way of example, the concentration and return electrodes may be disposed near the periphery of the footprint of the flow cell. In yet another embodiment, they are maybe disposed at substantially opposite ends of the flow cell. In yet another embodiment, the return electrode substantially circumscribes the footprint of the flow, with a centrally disposed collection electrode.

Effective interrogation of the sample within the flow cell is one desired result. It yet another optional aspect of this embodiment of this invention, one or more transport electrodes are provided, the transport electrodes being disposed on the substrate, and positioned between the first collection electrode and the array. In the preferred embodiment, there are at leas two transport electrodes, and further, the transport electrodes are of a different size, preferably wherein the ratio of larger to smaller is at least 2:1. In this way, the relatively large area subtended by the collection electrode may be progressively moved to smaller and smaller locations near the analytical region of the device. This arrangement both aids in transitioning from the relatively large area of the collection electrode, but the stepped nature of the embodiment reduces current density mismatches, and by utilizing a stepped, preferably monotonically stepped size reduction, more effective transportation and reduced burnout is achieved.

In yet another embodiment of device, an electronic device for performing biological operations comprises a support substrate, an array of microlocations disposed on the substrate, the array being formed within a region, a first collection electrode disposed on the substrate adjacent the array, and a second collection electrode disposed on the substrate, adjacent the array, and at least in part on the opposite side of the region. In the preferred embodiment, the collection electrodes have an area at least 80% of the area of the region of the array. In this way, the sample may be collected in a relatively large area adjacent the region containing microlocations, from which the DNA or other charged biological materials may be provided to the region.

In the one method for use of this device the collection electrode may first collect the materials, and then be placed repulsive relative to the collected material, thereby sweeping the material towards the region containing the array. The material may be transported in a wave manner over the array, permitting either interaction with a passive array or an electrically active array. Alternatively, the material may be moved over the region of the array, and effective maintained in that position by application of AC fields. This embodiment has proved capable of performance of repeat hybridizations, where material is move to and interacted with the array, after which it is moved out of the region, and preferably held by the collection electrode or on other electrode, after which it is moved to the array for a second, though possibly different, interaction.

In yet another embodiment of device design, a substantially concentric ring design is utilized. In combination, an electronic device for performing active biological operations includes a support substrate, an array of microlocations disposed on the substrate, a first counter electrode disposed on the substrate surrounding the array, and a collection electrode disposed on the substrate and disposed interior of the array. In the preferred embodiment, the first counter or return electrode is segmented, optionally having pathways resulting in the segmentation which serve as pathways for electrical connection to the array. In yet another variation of this embodiment, multiple rings are provided surrounding the array.

In yet another embodiment of this invention, a simple, preferably five component system is implemented in a flip chip arrangement for providing active biological diagnostics. The device comprises in combination a support substrate having first and second surfaces, and a via, pathway or hole between the first and second surfaces to permit fluid flow through the substrate, the first or second surfaces supporting electrical traces, a second substrate including at least a first surface, the first surface being adapted to be disposed in facing arrangement with the first or second surfaces of the first substrate and positioned near, e.g., under, the via, the second substrate including electrically conductive trees connecting to an array of microlocations, the array being adapted to receive said fluid through the via, pathway or hole, electrically conductive bumps interconnecting the electrical traces on the second surface of the support substrate and the electrical traces on the first surface of the second substrate, a sealant disposed between the second face of the support substrate and the first face of the second substrate, said sealant providing a fluidic seal by and between the first substrate and the second substrate, and a flowcell dispose on the first surface of the first substrate. This design is particularly advantageous in reducing the number of components in the device, and to improve manufacturing reliability.

In yet another embodiment, an electronic device for performing active biological operations comprises a support substrate having a first and second surface, and a via between the first and second surfaces to permit fluid flow through the substrate, a second substrate including at least a first surface, the first surface being adapted to be disposed in facing arrangement with the second surface of the first substrate, the second substrate including an array of microlocations, the array being adapted to receive said fluid, a sealant disposed between the second face of the support substrate and the first face of the second substrate, a source of illumination, and a waveguide having an input adapted to receive the illumination from the source, and an output adapted to direct the illumination to the array, the waveguide being substantially parallel to the support substrate, the illumination from the waveguide illuminating the array. In the preferred embodiment, the source of illumination is a laser, such as a laser bar. Such a device may utilize a support substrate which is flex circuit or a circuit board.

A novel, advantageous method of manufacture may be utilized with some or all of the embodiments. The method is particularly advantageous for the flip chip design the structure having a chip disposed adjacent a substrate, the substrate including a via therethrough, the structure being adapted to receive a fluid to be placed on the substrate, and to flow through the via down to the chip, at least a portion of the chip including an area to be free of sealant overcoat. Selection of sealant viscosity and materials may effectively result in effective coverage, good thermal contact between the substrate and the chip, and fluidic sealing. In the most preferred embodiment, the method may include use of a light-curable sealant which is cured with light during application. The steps in that process included affixing a chip to a subtle, exposing light to the device, onto the substrate, and through the via, down to the chip, providing a light curable, wickable sealant to the interface between the substrate and the chip, at least partially curing the sealant as a result of the exposure, whereby the sealant is precluded from flowing to said area to be free of sealant, and optionally, completing the cure of the sealant, such as by heat treatment In yet another embodiment, a system or chip includes a multi-site array with electrically repetitive site cell locations. Typically, the array is formed of rows and columns, most typically an equal number of rows and columns. The individual limit cells of the array of unit cells is selected by action of selectors such as a row selector and a column selector. The selector may be a memory, such as a shift register memory, or a decoder, or a combination of both. An input for address information receives addresses, typically from off-chip, though on chip address generators may be utilized. In the preferred embodiment, the row selectors comprise shift registers, either in a by one configuration, or in a wider configuration, such as a by four configuration. In operation, the selection registers are sequentially loaded with values indicating selection or not of a unit cell, and optionally, the value of output for that cell. Optionally, memory may be provided to retain those values so as to continue the output from the unit cell.

In one preferred embodiment of a unit cell, a symmetric arrangement is utilized. A first column select unit, preferably a transistor, and a first row select unit, also preferably a transistor, are in series relation between a first source, e.g., voltage and/or current source, and a node, typically a current output node. In the preferred embodiment, the column select transistor may be precisely controlled under application of a gate voltage such as from the column shift register memory. Preferably, the select units may differ from each other in their controllability, such as by varying the channel length in the control transistor. The channel lengths have been chosen so as to match the gain between the row and column transistors. Also, the long channel length provides the ability to control small currents with reasonable control signals. Thus, by application of potentials from the row selector and column selector, application of potential to the control gates results in output of current at the unit cell.

The unit cell circuit preferably further includes a second column select unit, preferably a transistor, and a second row select unit, also preferably a transistor, used in series relation between a second source, e.g., voltage and/or current source, and a node, typically the previously referred to node, i.e., a current output node. In the preferred embodiment, the first, source is a supply potential Vcc and the second source is a reference potential such as ground. Preferably the nodes are the same node, such that there is a series connection between Vcc and ground of the first column select unit and first row select unit, the node, and the second row select unit and the second column select unit.

In yet another aspect of the preferred embodiment, test circuitry is included. A first test transistor spans the first column select and first row select transistor. Likewise, a second test transistor spans the second column select and second row select transistor. Selective activation ensures continuity of the circuit. Alternatively, the test circuit function may be performed by special programming of the row and column transistors, e.g., turning on of the first and second row select and first and second column select transistors.

In yet another aspect of these inventions, the various devices may be decorated or covered with various capture sequences. Such capture sequences may be relatively short, such as where the collection electrode is a complexity reduction electrode. Further, relatively longer capture sequences may be used when further specificity or selectivity is desired These capture sequences may preferably be included on the collection electrodes, or intermediate transportation electrodes.

Accordingly, it is an object of this invention to provide an active biological device having reduced costs of manufacture yet consistent with achieving a small size microlocation.

It is yet another object of this invention to provide devices which provide increased functionality.

It is yet a further object of this invention to provide devices which achieve a high degree of functionality and operability with fewer parts than known to the prior art.

It is yet a further object of this invention to provide devices which are easier to manufacture relative to the prior art.

DETAILED DESCRIPTION OF THE INVENTION

Figure 1A:
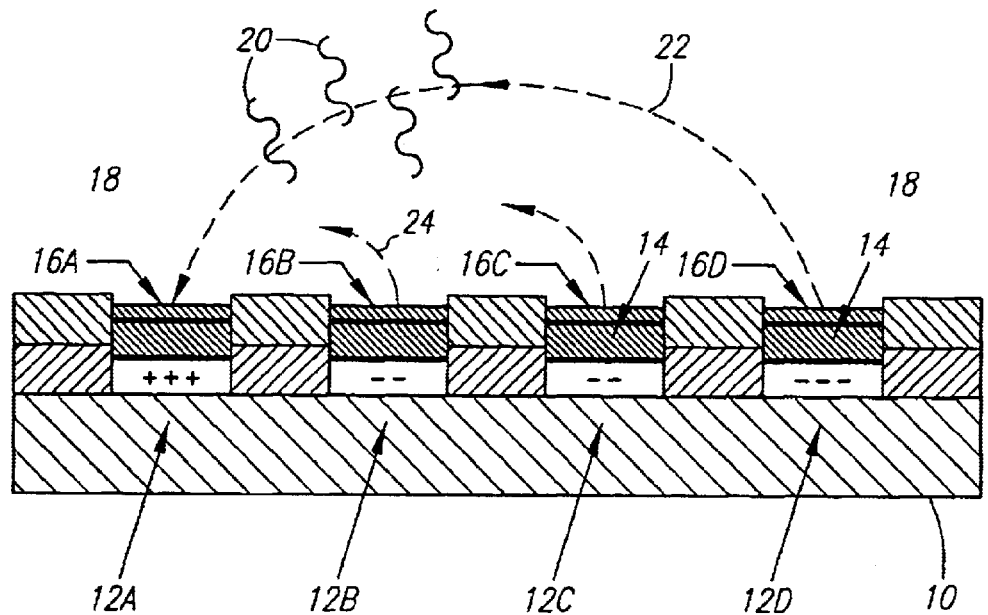
FIGS. 1A and 1B show an active, programmable electronic matrix device (APEX) in crosssection (FIG. 1A) and in perspective view (FIG. 1B).
Figure 1B:
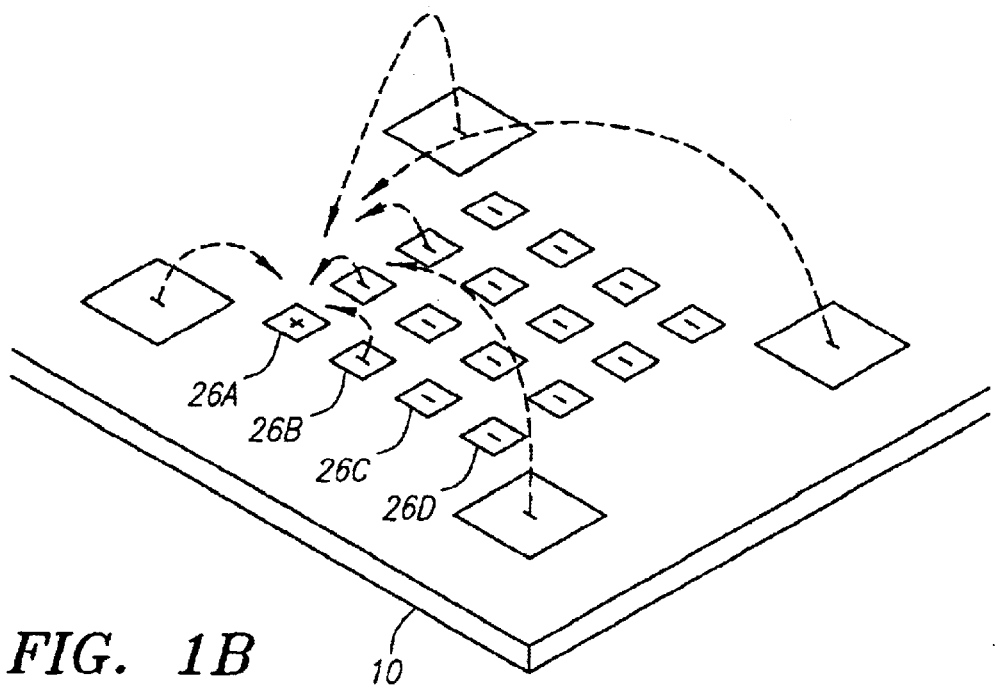

FIGS. 1A and 1B illustrate a simplified version of the active programmable electronic matrix hybridization system for use with this invention. Generally, a substrate 10 supports a matrix or array of electronically addressable microlocations 12. For ease of explanation, the various microlocations in FIG. 1A have been labeled 12A, 12B, 12C and 12D. A permeation layer 14 is disposed above the individual electrodes 12. The permeation layer permits transport of relatively small charged entities through it, but limits the mobility of large charged entities, such as DNA, to keep the large charged entities from easily contacting the electrodes 12 directly during the duration of the test. The permeation layer 14 reduces the electrochemical degradation which would occur in the DNA by direct contact with the electrodes 12, possibility due, in part, to extreme pH resulting from the electrolytic reaction. It further serves to minimize the strong, non-specific adsorption of DNA to electrodes. Attachment regions 16 are disposed upon the permeation layer 14 and provide for specific binding sites for target materials. The attachment regions 16 have been labeled 16A, 16B, 16C and 16D to correspond with the identification of the electrodes 12A–D, respectively.

In operation, reservoir 18 comprises that space above the attachment regions 16 that contains the desired, as well as undesired, materials for detection, analysis or use. Charged entities 20, such as charged DNA are located within the reservoir 18. In one aspect of this invention, the active, programmable, matrix system comprises a method for transporting the charged material 20 to any of the specific microlocations 12. When activated, a microlocation 12 generates the free field electrophoretic transport of any charged functionalized specific binding entity 20 towards the electrode 12. For example, if the electrode 12A were made positive and the electrode 12D negative, electrophoretic lines of force 22 would run between the electrodes 12A and 12D. The lines of electrophoretic force 22 cause transport of charged binding entities 20 that have a net negative charge toward the positive electrode 12A. Charged materials 20 having a net positive charge move under the electrophoretic force toward the negatively charged electrode 12D. When the net negatively charged binding entity 20 that has been functionalized contacts the attachment layer 16A as a result of its movement under the electrophoretic force, the functionalized specific binding entity 20 becomes covalently attached to the attachment layer 16A.

Figure 2:
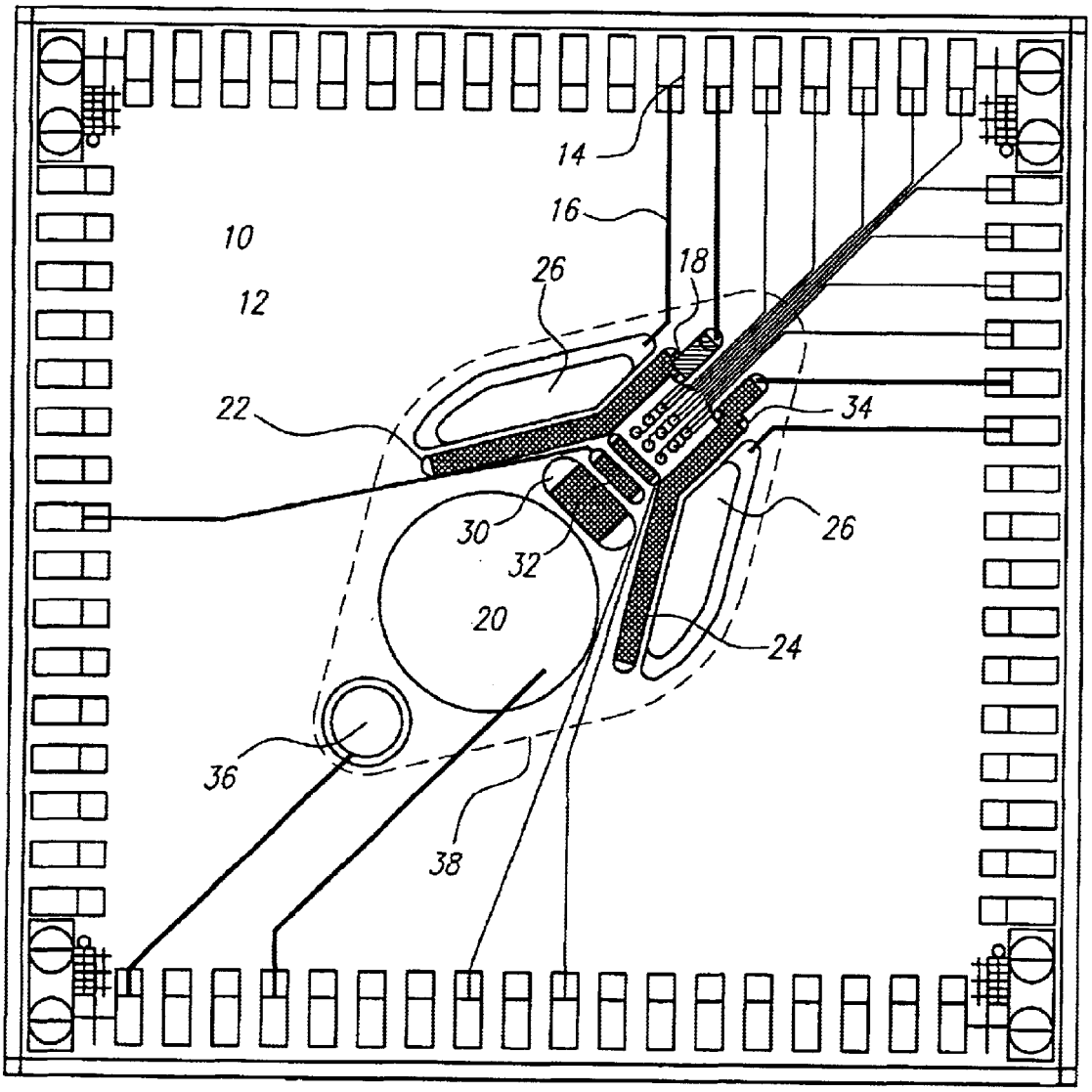
FIG. 2 is a plan view of an embodiment of the invention which utilizes varying sized electrode regions.

FIG. 2 is a plan view of one embodiment of the invention which utilizes focusing electrodes, and optionally, transport electrodes. The device 10 includes a substrate 12, which may be of any sufficiently rigid, substantially nonconductive material to support the components formed thereon. The substrate 12 may be flex circuit (e.g., a polyimide such as DuPont Kapton, polyester, ABS or other such materials), a printed circuit board or a semiconductive material, preferably with an insulative overcoating. Connectors 14 couple to traces 16, which in turn, couple to other electrical components of the system. These components may be any form of conductor, such as copper, or gold, or any other conductor known to those skilled in the art. Array 18 is preferably of the form described in connection with FIG. 1.

A first collection electrode 20 and counter electrodes 26 are disposed on the substrate 20. These generally fit within the footprint of the flow cell 38, and comprise a relatively large percentage thereof preferably at least substantially 40%, and more preferably substantially 50% or substantially 60%. The counter electrode and return electrode are preferably disposed at or near the periphery of the flow cell footprint, and may substantially circumscribe, e.g., to 80%, the footprint perimeter. Typically, the collection electrode and counter electrodes are disposed on the substrate so that the electrophoretic lines of force are significant over substantially all of the flow cell volume. By way of example, the concentration and return electrodes may be disposed near the periphery of the footprint of the flow cell. In yet another embodiment, they are maybe disposed at substantially opposite ends of the flowcell. In yet another embodiment, the return electrode substantially circumscribes the footprint of the flow, with a centrally disposed collection electrode. The relatively large percent of coverage of the flow cell footprint and its position aids in electrophoretic interrogation of the flow cell contents.

Focusing electrodes 22, 24 are disposed on the substrate 12 to aid in focusing materials collected on the collection electrode 20 to the array 18. The focusing electrodes 22, 24 are preferably disposed in a mirror-image, "Y" shaped pattern, the open end encompassing, at least in par; the collection electrode 20.

Transport electrodes 30, 32, 34 are optionally included. These electrodes of monotonically decreasing size are shown. A first transport electrode 30 is relatively smaller than the collection electrode 20, the second transport electrode 32 is relatively smaller than the first transport electrode 30, and the third transport electrode is yet smaller still. The differential sizing serves to reduce current density mismatches between locations, and aids in reducing or eliminating bum-out which may result if too great a current density mismatch exists. Transport efficiently is maximized. The ratio of sizes of larger to smaller is preferably substantially 2 to 1, more preferably 3 to 1, and may be even greater, such as 4 to 1 or higher.

Figure 3:
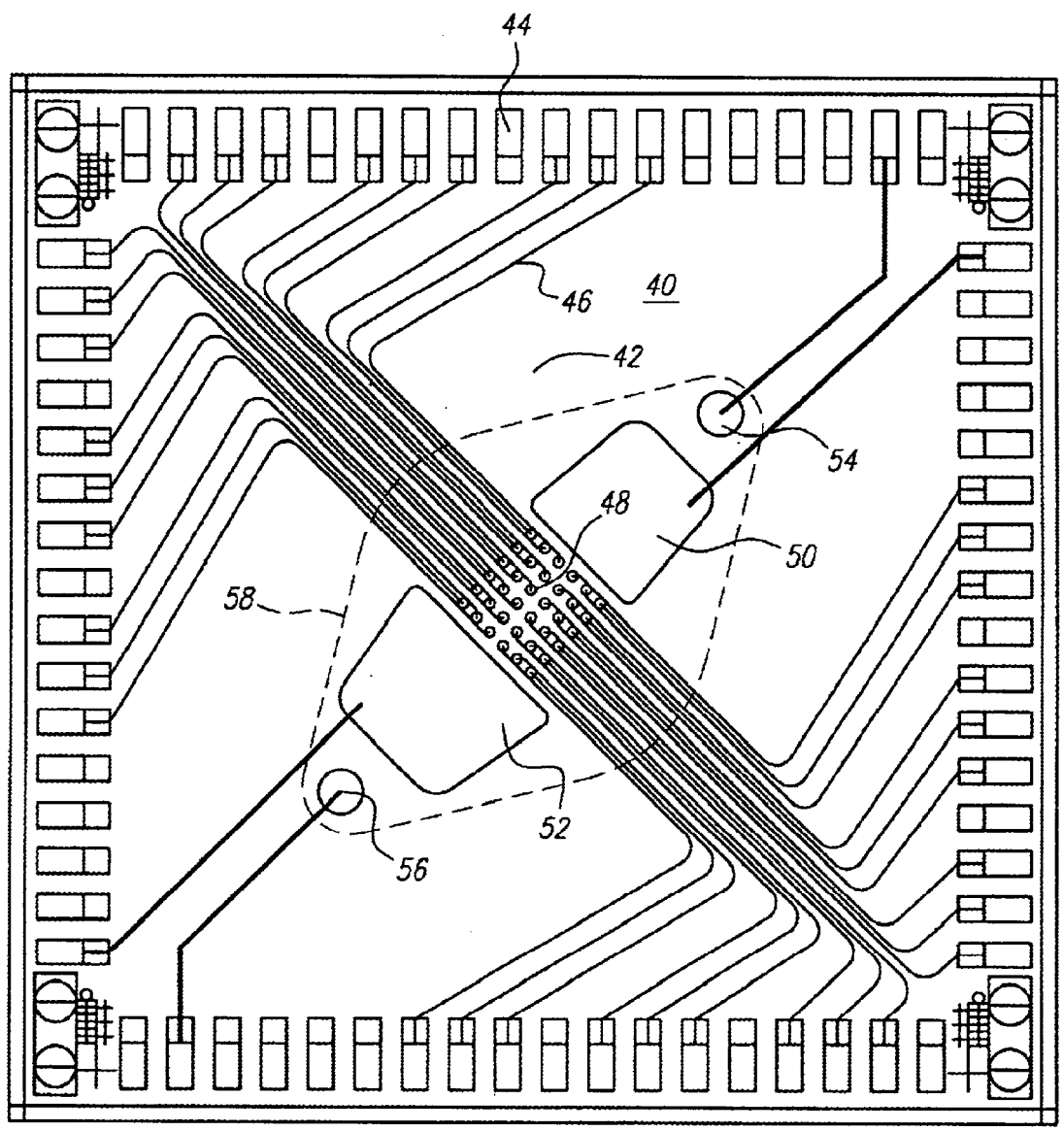
FIG. 3 is a plan view of an embodiment of the invention which utilizes a concentration electrode and paired return electrode, useful in methods which effectively transport charged biological material in a wave or sweeping motion across microlocations.

One field-shaping protocol is as follows:

embodiment of FIG. 3, first collection electrode 40 is a trapezoid, which has a long base adjacent to and parallel to one side of the array 48. The second collection electrode 52 is disposed on the other side of the array 48, and is similarly (though not necessarily identically) shaped and sized. Optionally, the electrodes 50, 52 may be of different sizes, such as where the area of the first collection electrode 50 is approximately 10% larger (optionally approximately 20% larger) than the second collection electrode 52. Input port electrodes 54 and port electrode 56 are optionally included on the substrate 42, within the footprint of the flow cell 58.

In operation, the flow cell contents are interrogated by placing or biasing one of the first and second collection electrodes 50, 52 attractive (typically positive) to the materials to be collected. Once collected, the materials may be transported away from the first collection electrode 50 towards the stray 48. The materials may be effectively held in place over the array 48, such as by application of AC fields between the electrodes 50, 52. Then materials may be transported to the other electrode 50, 52 or may be repeatedly reacted by moving materials from the array 48 to the electrodes 50, 52. Optionally, the microlocations of the array 48 may be electrically active or passive.

Figure 4:
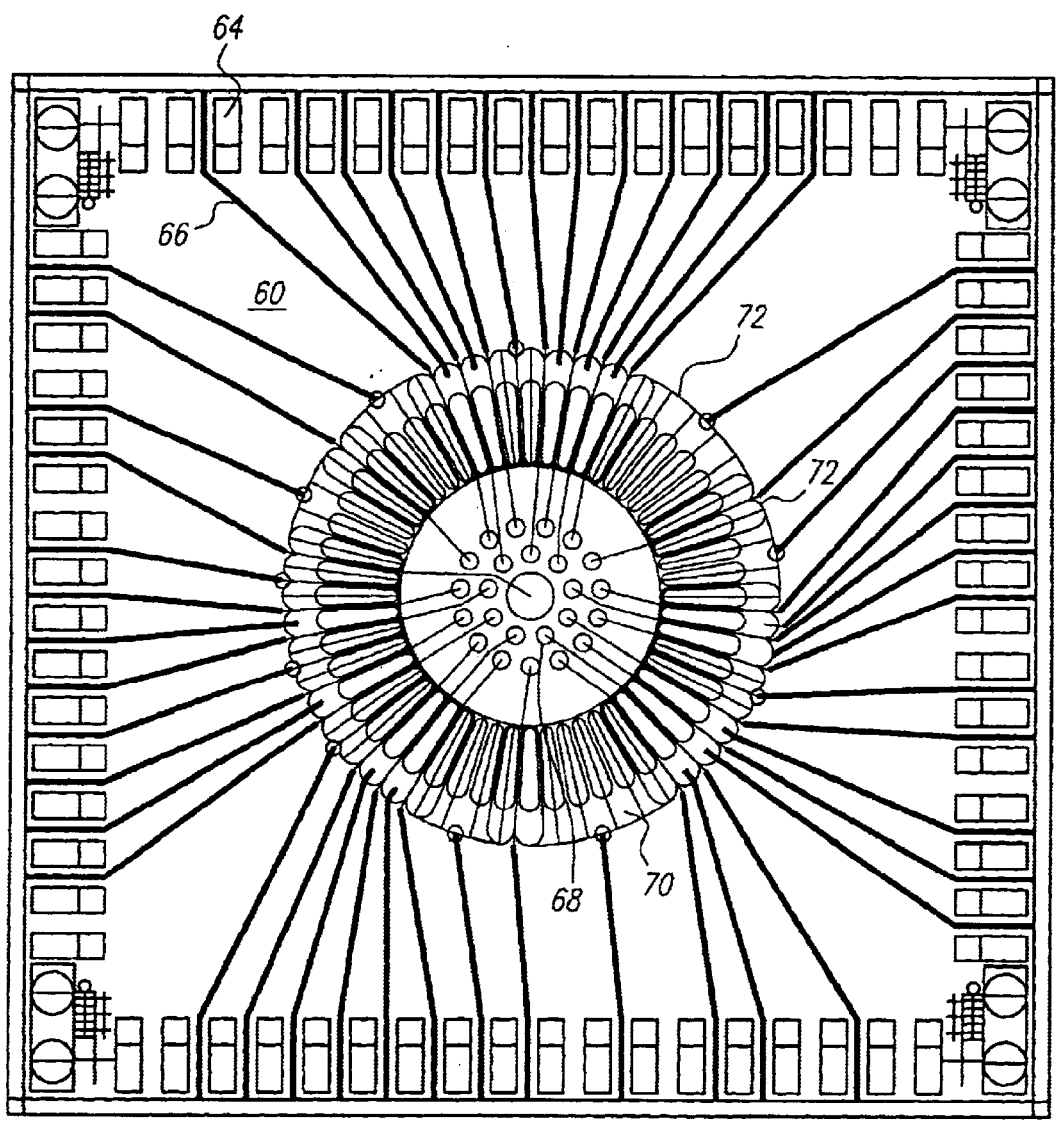
FIG. 4 is a plan view of an embodiment of the invention which utilizes a substantially circular arrangement, with a substantially centrally disposed concentration electrode.

FIG. 4 is a plan view of a concentric ring electrode embodiment. The device 60, substrate 62, connectors 64, traces 66 and array 68 are as previously described, with the exception that the array 68 maybe arranged concentrically. A concentric return electrode 70 and central concentration electrode 72, preferably round, coact to concentrate material at electrode 72, and then to move it over or position it above the array 72.

In the embodiments of FIGS. 2, 3 and 4, capture sequences or probes may be disposed on the devices. Pref-

| Negative Bias | Positive Bias | Current | Bias Time |
| --- | --- | --- | --- |
| Counter Electrode 26 | 1st Collection Electrode 20 | 75 | 30 sec. |
| Focusing Electrode 26 (−0.2) 1st Collection Electrode 20 | 1st Transport Electrode 30 | 25 | 90 sec. |
| Focusing Electrode 26 (−0.2) 1st Transport Electrode 30 | 2nd Transport Electrode 32 | 5 | 180 sec. |
| Focusing Electrode 26 (−0.2) 1st Transport Electrode 30 2nd Transport Electrode 32 | 3rd Transport Electrode 34 | 3 | 420 sec. |
| Focusing Electrode 26 (−0.2) 2nd Transport Electrode 32 3rd Transport Electrode 34 | Row 3 | 1.5 (500 n/pad) | 120 sec. |
| Focusing Electrode 26 (−0.2) 2nd Transport Electrode 32 3rd Transport Electrode 34 | Row 2 | 1.5 (500 n/pad) | 120 sec. |
| Focusing Electrode 26 (−0.2) 2nd Transport Electrode 32 3rd Transport Electrode 34-- | Row 1 | 1.5 (500 n/pad) | 120 sec. |

In operation, the collection electrode 20 and return electrode 26 serve to collect charged biological materials to the collection electrode. The transport electrodes 30, 32, 34, preferably in combination with the focusing electrodes 26 serve to transport the materials from the collection electrode 20, which may now be biased repulsive, while providing a force lateral to the direction of transportation thereby centrally concentrating material.

FIG. 3 is a plan view of another embodiment of this invention. As with FIG. 2, a device 40 includes a substrate 42, connectors 44, traces 46 and an array of microlocations 48. The comments made for FIG. 2 and others apply to corresponding structures in other figures. FIG. 3 departs from FIG. 2 in the inclusion of a first collection electrode 50, being disposed at least in part adjacent the array 48. In the erably these are at least on the collection or concentration electrodes; Optionally, different sequences are disposed on different devices such as the transport electrode 30, 32 and 34 of FIG. 2.

Figure 5A:
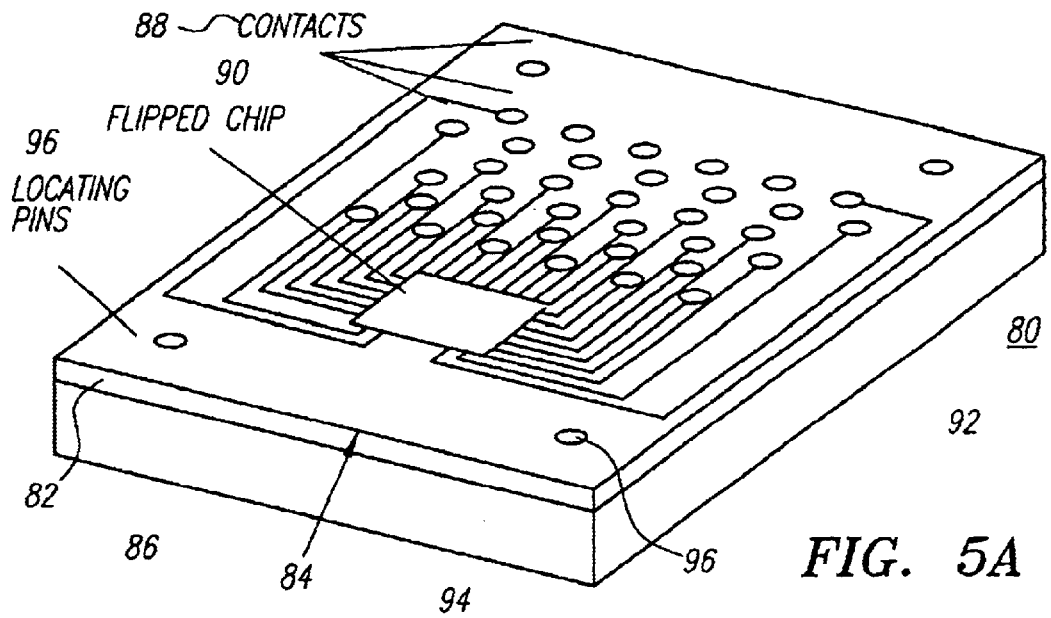
FIGS. 5A, 5B, and 5C show perspective views of the bottom and top and via (in top view), respectively, of a flip-chip system.
Figure 5B:
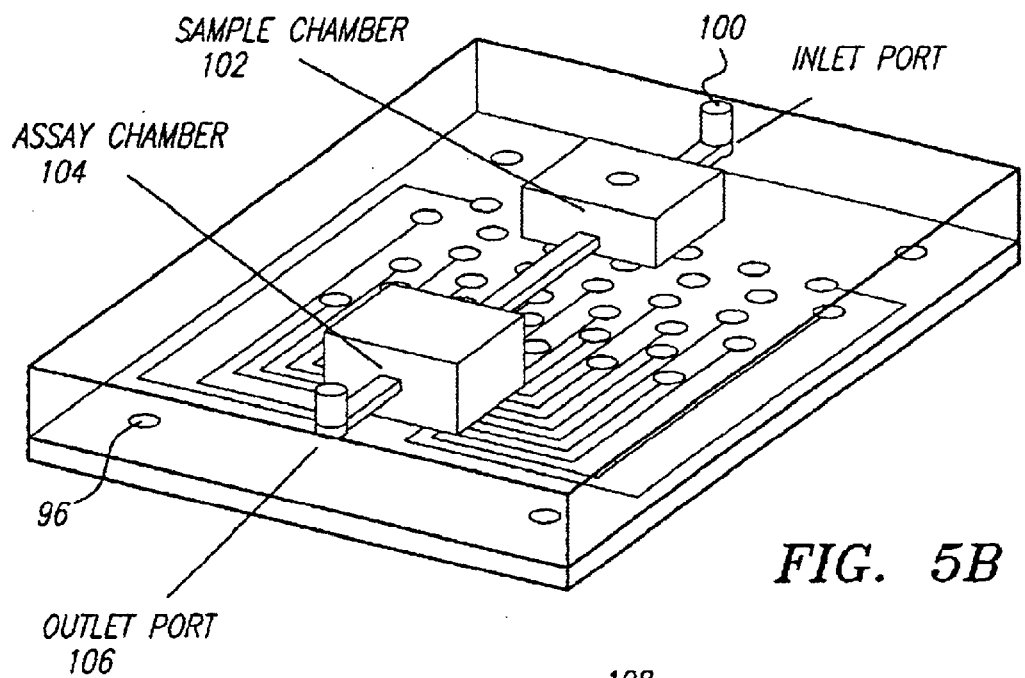
Figure 5C:
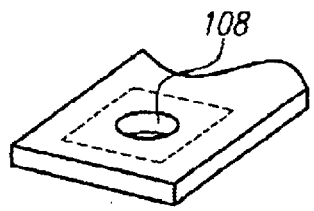
Figure 6A:
FIG. 6A is a cross-sectional view of a flip-chip system showing an inlet port and sample chamber.
Figure 6B:
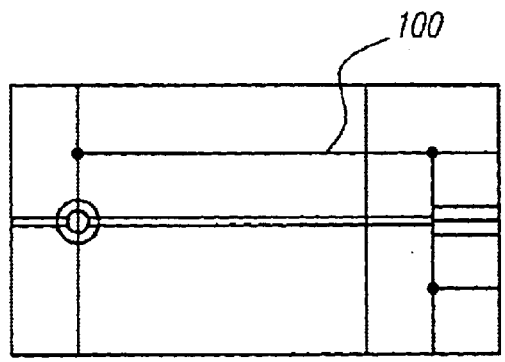
FIG. 6B is a top view of the flip-chip system shown in FIG. 6A.
Figure 6C:
FIG. 6C is a side view of the flip-chip system shown in FIG. 6A.
Figure 6D:
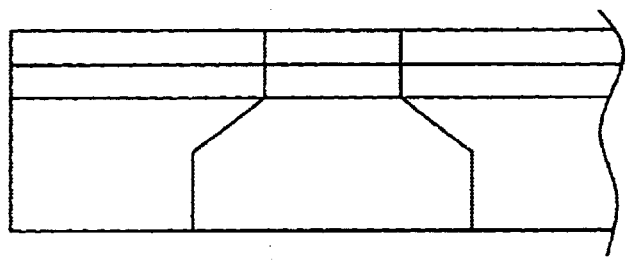
FIG. 6D is an enlarged detail view of the inlet port shown in FIG. 6A.
Figure 6E:
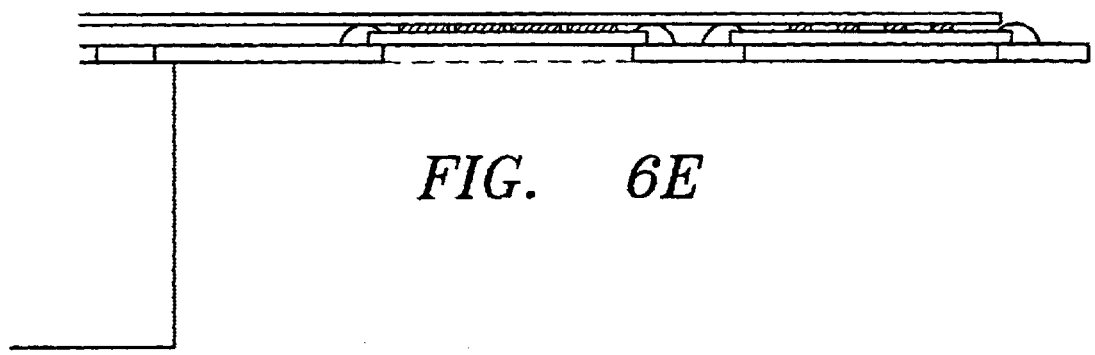
FIG. 6E is a side view showing a flip-chip system having multiple flip-chips.

FIGS. 5A, 5B and 5C show perspective views of the bottom and top and via 108 in top view, respectively, of a flip-chip system. A device 80 includes a support substrate 82 having a first surface 84 and a second surface 86, which may be of materials suitable for the function of support and conduction, such as flex circuitry, printed circuit board or semiconductive material. Contacts 88 lead to traces 90, which lead to the second substrate 92. Contacts, such as bump contacts, e.g., solder bumps, indium solder bumps, conductive polymers, silver filled epoxy, provide electrical contact between traces 90 and the chip or substrate 92. A sealant is disposed between the second surface 86 of the support substrate 82 and the first surface 94 of the second substrate 92. An inlet port 100 may be in conductive relation to a sample chamber 102, which yet further leads to the assay chamber 104, and on to the outlet port 106. FIG. 5C shows a perspective view of the support 82 and the via 108 formed through it. The second substrate 92 is shown in dashed lines, which is disposed below the substrate 82 in the view of FIG. 5C.

Figure 8:
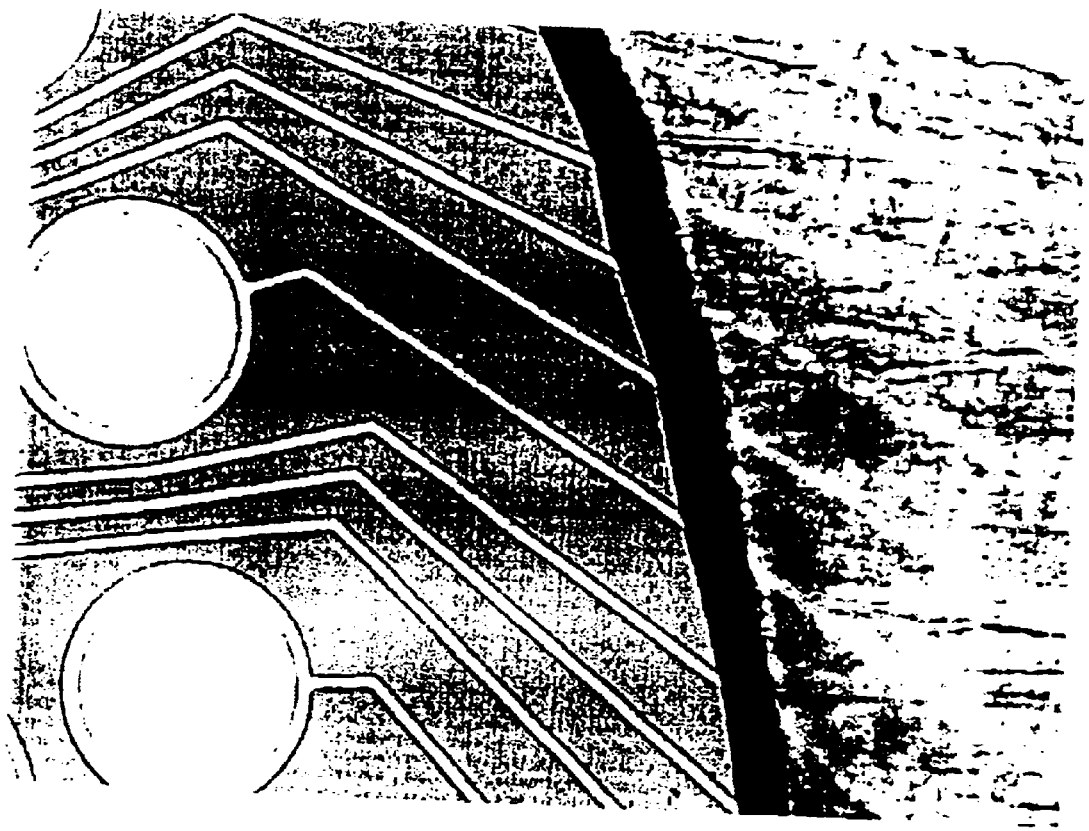
FIG. 8 is a microphotograph of barrier wall for the Norland 83H dan using a 1300 J/s fiber bundle source shadow masked with the flex circuit (Flex polyimide removed).

In operation, a sample is provided to the inlet port 100 and passed to the sample chamber 102. Thereafter, the sample flows to the assay chamber 104. Solution containing sample flows down through via 108. A space comprising the via 108, bounded on the bottom by the se substrate 92, with sealant or adhesive between the second surface 86 of the support substrate 82, and first surface 94 of second substrate 92. In the preferred method of manufacture, a light curable sealant is wicked or otherwise provided to that interface, and light is provided through the via 108. A dam is formed, stopping the advance of the sealant, thereby maintaining the array, e.g., 18, free from sealant or adhesive. See FIG. 8 for a microphotograph showing the sealant free area of the array, the cured leading edge of the dam and sealant on the exterior portions of the device.

Figure 7:
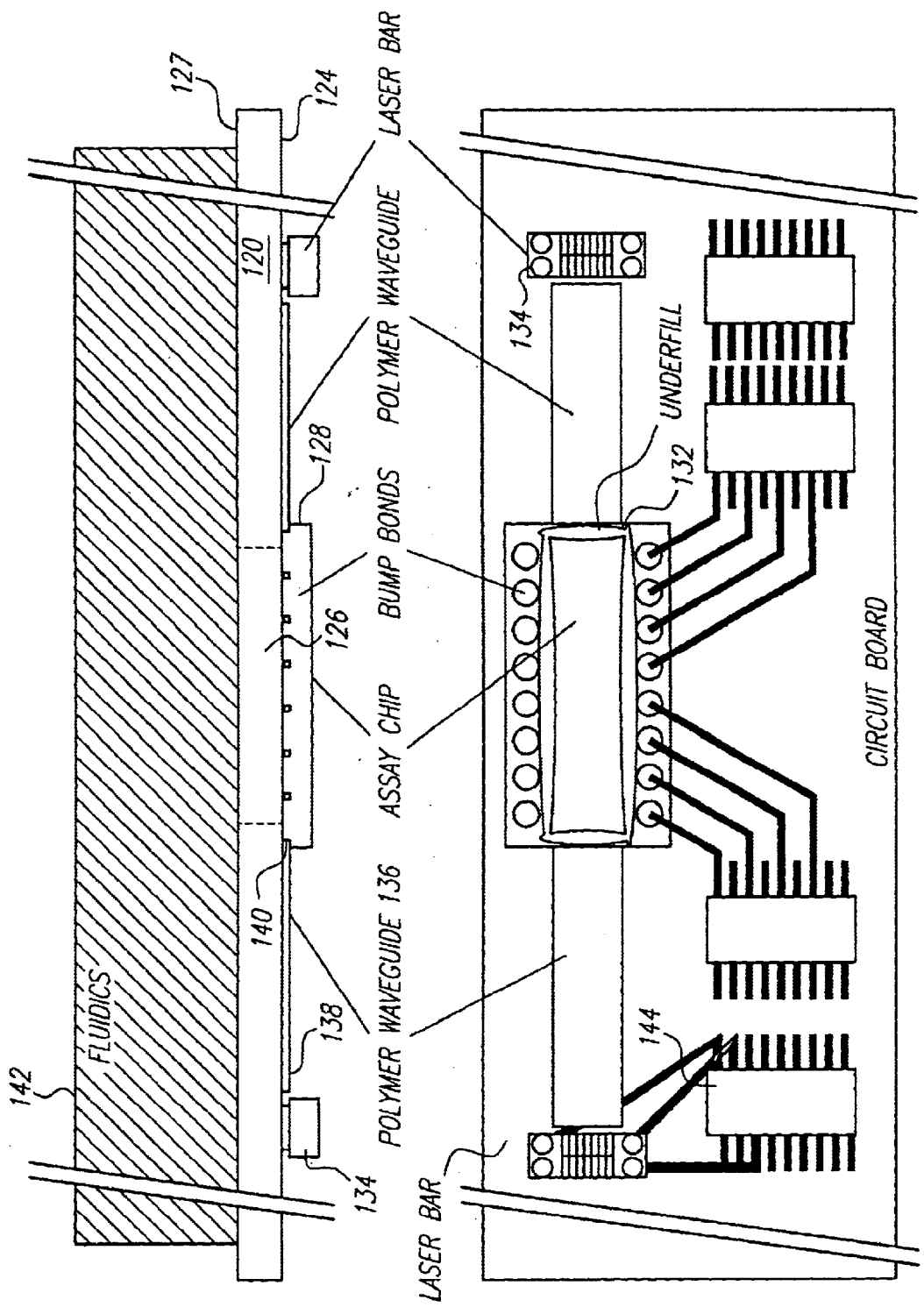
FIG. 7 shows side and plan views of an edge illuminated system in one embodiment of this invention.

FIG. 7 is a cross-sectional and plan view of an edge illuminated, flip-chip system in accordance with one embodiment of the invention. A support substrate 120 is generally planar, and includes a first face 122 and a second face 124. A via 126 permits fluid or solution flow from above the support substrate 120 to the second substrate 128, particularly to the first surface 130 of the second substrate 128. Sealant 132 is provided between the second surface 124 of the support substrate 120 and the second substrate 128. The sealant 132 provides a preferably fluid tight-seal, so as to permit fluid flow to the array on the second substrate 128. A source of illumination 134, such as a laser bar, illuminate the array on the second substrate 128. Preferably, the system includes in a waveguide 136 with an input 138 adapted to receive illumination from the source 134, and to provide illumination via output 140. The waveguide 136 is preferably co-planar with the support substrate 120, and may be secured to it, such as by being adhered to the second surface 124 of the support substrate 120. Electronics 144 may be included to control the system. Fluidics 142 may be provided in combination with the system to aid in provision of the sample to the second substrate 128.

Figure 9:
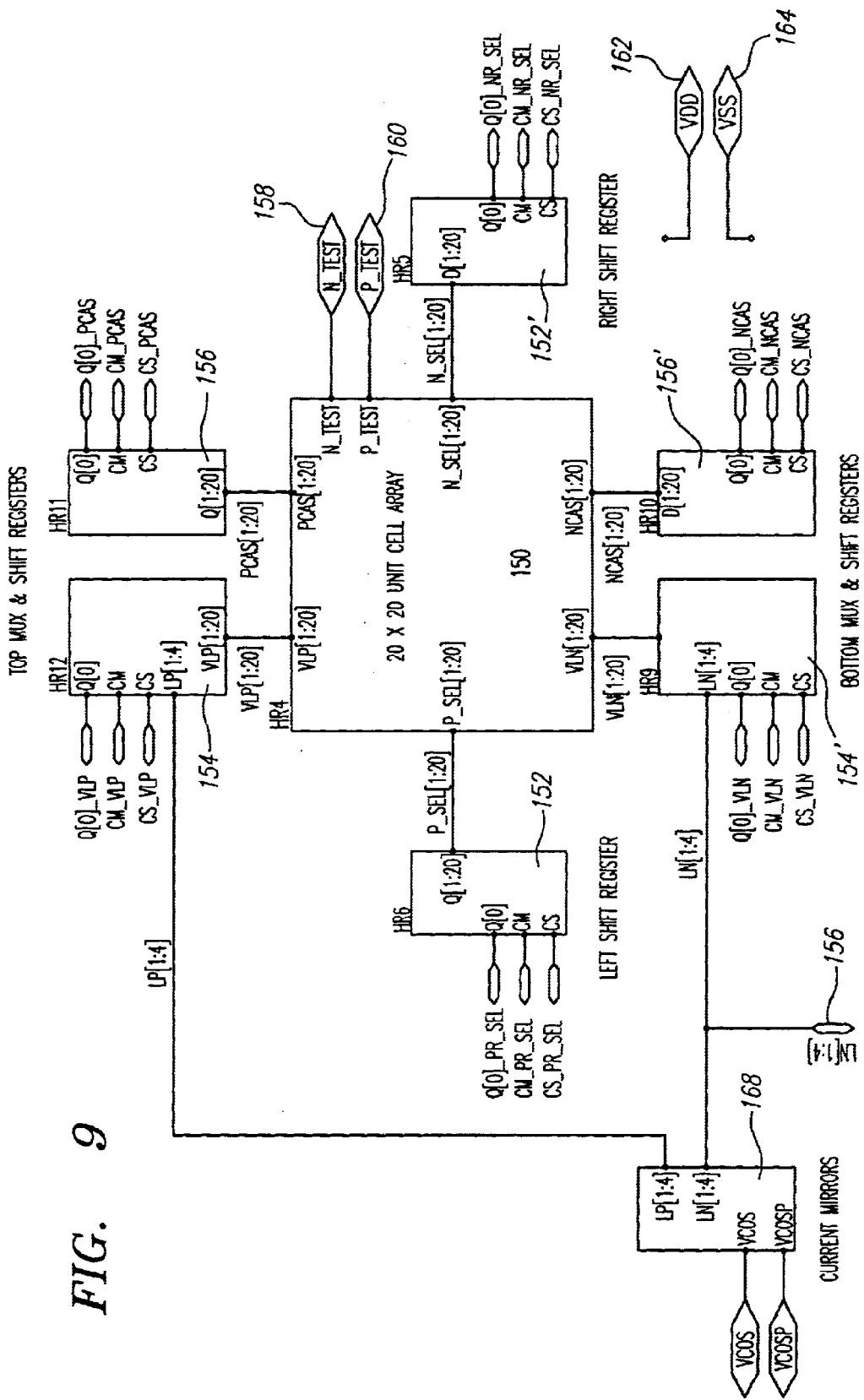
FIG. 9 is a block diagram drawing of a multiple unit cell array system.

FIG. 9 is a block diagrammatic depiction of a multiple unit cell array. In yet another embodiment, a system or chip includes a multi-site array with electrically repetitive site cell locations. Typically, the array is formed of rows and columns, most typically an equal number of rows and columns. The individual unit cells of the array of unit cells is selected by action of selectors such as a row selector and a column selector. The selective may be a memory, such as a shift register memory, or a decoder, or a combination of both. An input for address information receives addresses, typically from off-chip, though on chip address generators may be utilized. In the preferred embodiment, the row selectors comprise shift registers, either in a by one configuration, or in a wider configuration, such as a by four configuration. In operation, the selection registers are sequentially loaded with values indicating selection or not of a unit cell, and optionally, the value of output for that cell. Optionally, memory may be provided to retain those values so as to continue the output from the unit cell.

Figure 10:
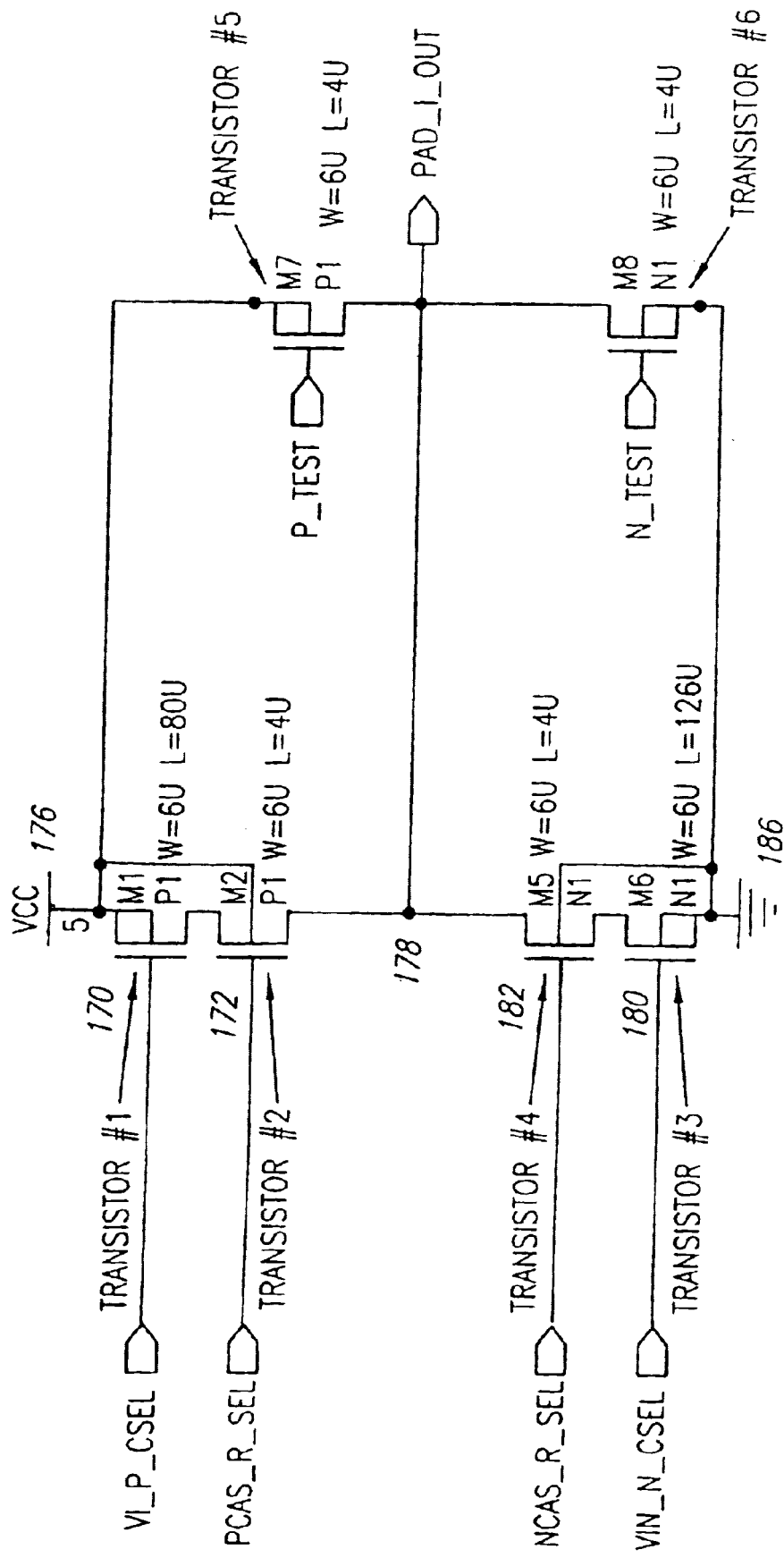
FIG. 10 is a circuit diagram of a unit cell usable with the system of FIG. 9.

FIG. 10 is a circuit schematic for a driving circuit for a unit cell in one embodiment of this invention. In one preferred embodiment of a unit cell, a symmetric arrangement is utilized. A first column select unit, preferably a transistor, and a first row select unit, also preferably a transistor, are in series relation between a first source, e.g., voltage and/or current source, and a node, typically a current output node. In the preferred embodiment, the column select transistor may be precisely controlled under application of a gate voltage such as from the column shift register memory. Preferably, the select units may differ from each other in their controllability, such as by varying the channel length in the control transistor. Thus, by application of potentials from the row selector and column selector, application of potential to the control gates results in output of current at the unit cell.

The unit cell circuit may further include a second column select unit, preferably a transistor, and a second row select unit, also preferably a transistor, used in series relation between a second source, e.g., voltage and/or current source, and a node, typically the previously referred to node, i.e., a current output node. In the preferred embodiment, the first source is a supply potential Vcc and the second source is a reference potential, such as ground. Preferably the nodes are the same node, such that there is a series connection between Vcc and ground of the first column select unit and first row select unit, the node, and the second row select unit and the second column select unit.

In yet another form of the circuit, or alternatively, a different mode of operation of the circuit shown in FIG. 10, the circuit may be tested for continuity by simultaneously activating each of the first and second row and column select transistors 170, 172, 180 and 182. In this way the source 176 and sink 186 are directly conductively connected.

In yet another aspect of the preferred embodiment, test circuitry is included. A first test transistor spans the first column select and first row select transistor. Likewise, a second test transistor spans the second column select and second row select transistor. Selective activation ensures continuity of the circuit. This current minor circuitry provides for efficient and effective operation.

Figure 11:
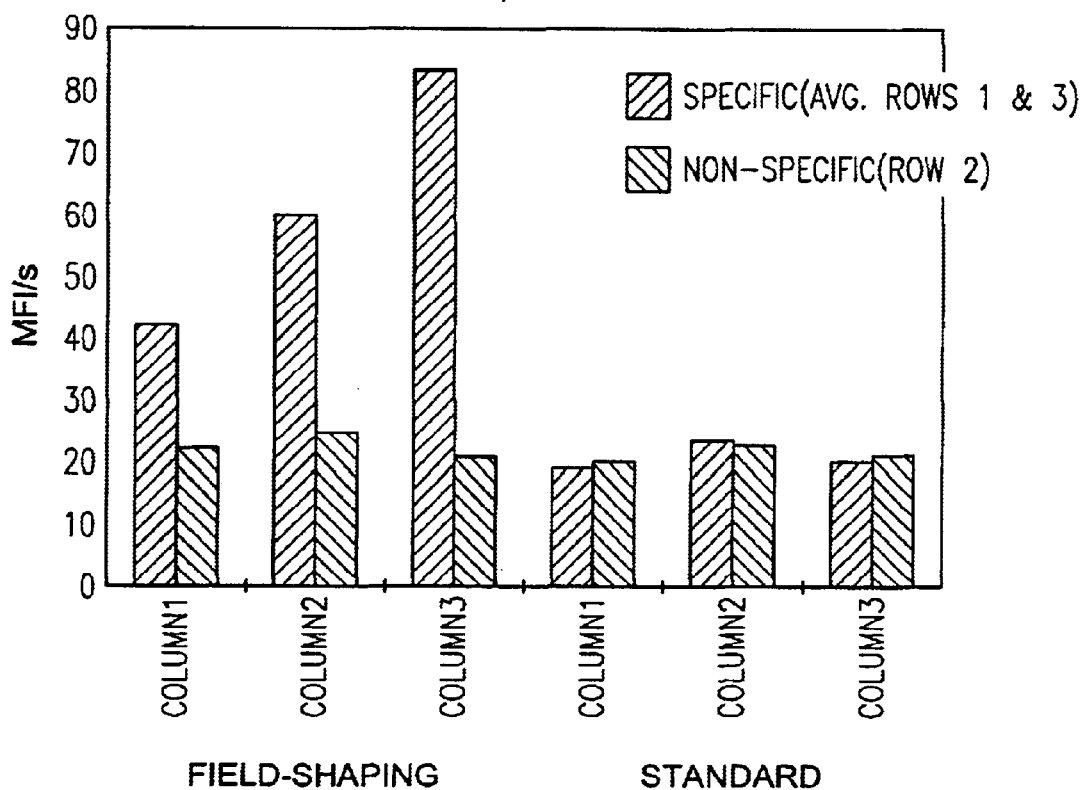
FIG. 11 is a graph of hybridization as a function of specific and non-specific hybridization for field-shaping and for no use of field shaping.

FIG. 11 shows a graph of electronic hybridization utilizing the chip of FIG. 2. The graph shows the fluorescent intensity, in MFI/s as a function of column number. The three bar graphs labeled column 1, column 2 and column 3 utilize field shaping, and show specific hybridization on the left bar graph in comparison to non-specific hybridization on the adjacent right hand column. The three couplets of bar graphs labeled column 1, column 2 and column 3 above the designator "standard" show the same system but without field shaping. The discrimination between specific versus non-specific binding is significantly less than in the case where field shaping is utilized.

The sequences were ATA5/ATA7/biotin, and 10 pM RCA5/BTR.

Figure 12:
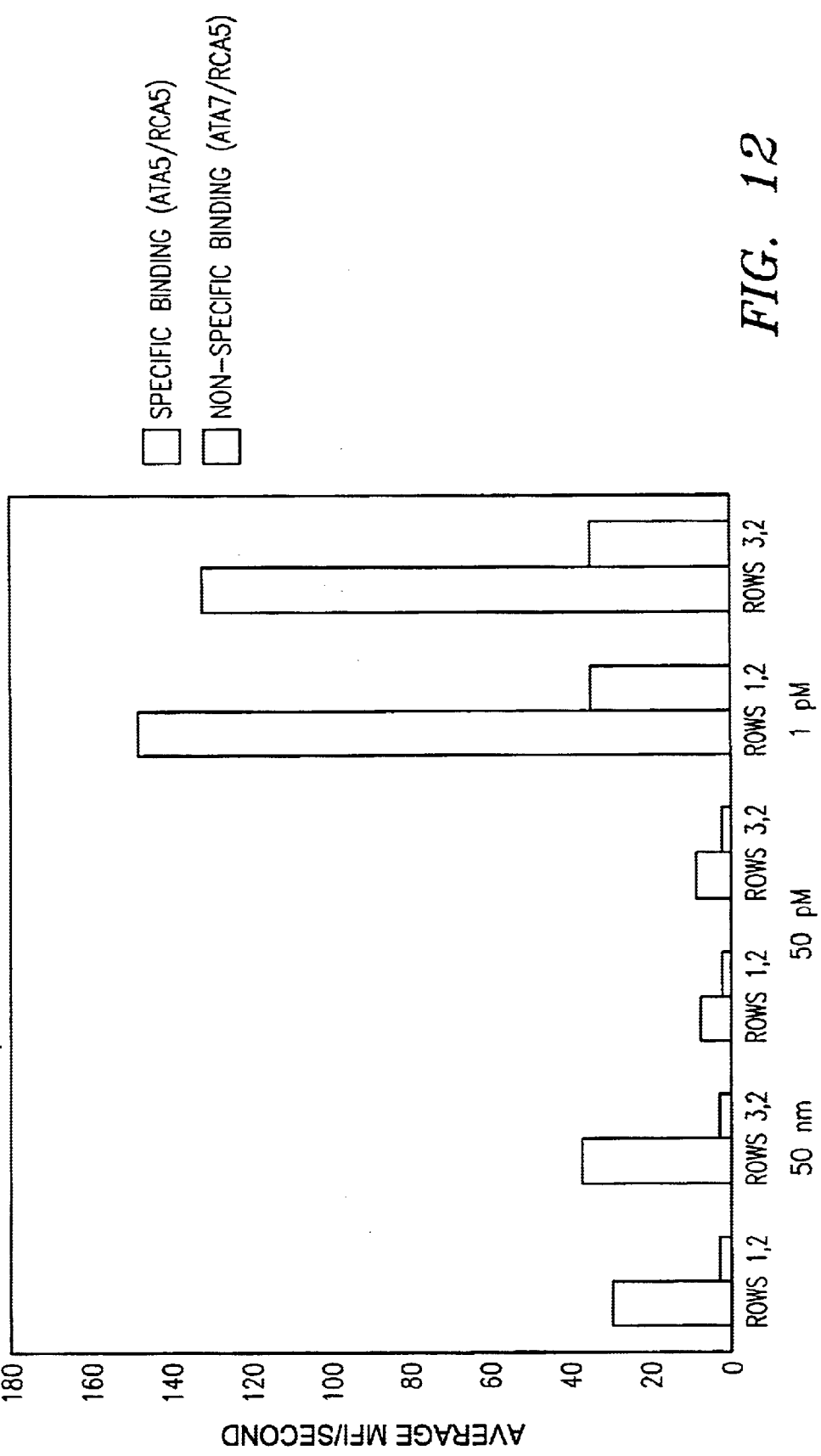
FIG. 12 is a graph of Average MFI/s at various concentrations for the embodiment of FIG. 2, at various concentrations RCA5 BTR Reporter in 50 mM histidine, showing Specific/Non-Specific Binding After Washing.

FIG. 12 shows a graph of experiments performed with the system as shown in FIG. 2. The y-axis shows the average MFI PER$^2$, and the x-axis shows various rows of various concentrations. The first couplet of paragraphs shows a 50 nM concentration of RCA5 BTR reporter in 50 mM histidine, and depicting the specific/non-specific binding after washing. The first couplet shows rows 1 and 2 comparing the specific binding (ATA5/RCA5) to the non-specific binding (ATA7/RCA5), showing a 12:1 and 50:1 improvement. The middle couplets of bar graphs show a 50 pM concentration of RCA5 BTR reporter and shows a 3.9:1 and 4.9:1 ratio of specific binding to non-specific binding signal intensity. The last set of couplet bar graphs shows a 1 pM concentration of RCA5 BTR reporter and shows a 4.4:1 and 4.0:1 ratio of specific binding to non-specific binding.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

We claim:

1. An electronic device for performing biological operations comprising:
   a support substrate,
   an array of microlocations disposed on the substrate, the array of microlocations comprising electronically addressable electrodes,
   a first collection electrode disposed on the substrate and adjacent to a first side of the array of microlocations,
   a second collection electrode disposed on the substrate and adjacent to a second side of the array of microlocations, the second side of the array being opposite of the first side such that the array of microlocations is disposed between the first collection electrode and the second collection electrode; and
   a flow cell, the flow cell adapted to be supported on the substrate.

2. The electronic device for performing active biological operations of claim 1 wherein the collection electrode is a complexity reduction electrode.

3. The electronic device for performing active biological operations of claim 1 further including focusing electrodes.

4. The electronic device for performing active biological operations of claim 1 wherein the flow cell defines a footprint such that the combined area of the first collection electrode and second collection electrodes in proportion to the footprint of the flow cell is at least 50%.

5. The electronic device for performing active biological operations of claim 1 wherein the flow cell defines a footprint such that the combined area of the first collection electrode and second collection electrodes in proportion to the footprint of the flow cell is at least 60%.

6. The electronic device for performing active biological operations of claim 1 wherein the flow cell includes an inlet.

7. The electronic device for performing active biological operations of claim 1 wherein the flow cell includes an outlet.

8. A method for analysis of a biological sample utilizing an electronic device for performing active biological operations, the device including a support substrate, an array of microlocations disposed on the substrate, the array of microlocations comprising electronically addressable electrodes a first collection electrode disposed on the substrate and adjacent to a first side of the array microlocations, and a second collection electrode disposed on the substrate and adjacent a second side of the array of microlocations, the second side of the array being opposite of the first side such that the array of microlocations is disposed between the first collection electrode and the second collection electrode, the method comprising the steps of:
   providing the sample to the device,
   placing the first collection electrode attractive relative to charged biological materials, thereby concentrating charged biological materials on the first collection electrode,
   placing the second collection electrode attractive to charged biological materials, thereby transporting said charged biological materials from the first collection electrode towards the second collection electrode, and over at least a portion of said array of microlocations disposed on the substrate, whereby interaction between the charged biological materials and the array occurs.

9. The method for analysis of a biological sample of claim 8 utilizing an electronic device for performing active biological operations, wherein the electrodes of the array are maintained electrically passive.

10. The method for analysis of a biological sample of claim 8 utilizing an electronic device for performing active biological operations, wherein the electrodes of the array are electrically active to facilitate interaction between the array and the charged biological material.

11. The method for analysis of a biological sample of claim 8 utilizing an electronic device for performing active biological operations, wherein the charged biological material is moved over the array as a wave.

12. The method for analysis of a biological sample of claim 8 utilizing an electronic device for performing active biological operations, wherein the charged biological material is moved over the array and held in place over the array.

13. The method for analysis of a biological sample according to claim 8 further comprising the step of applying an alternating current field between the first and second collection electrodes so as to hold the charged biological materials over the array.

14. The method for analysis of a biological sample according to claim 8, wherein when the second collection electrode is placed attractive relative to charged biological material, the first collection electrode is placed repulsive relative to charged biological material, thereby concentrating charged biological species on the second collection electrode.

15. The method for analysis of a biological sample according to claim 8 further comprising the additional steps of placing the second collection electrode repulsive relative to charged biological material and placing the first collection electrode attractive relative to charged biological material, thereby concentrating charged biological species on the first collection electrode.

* * * * *